United States Patent [19]

Planck

[11] Patent Number: 4,850,999
[45] Date of Patent: Jul. 25, 1989

[54] FLEXIBLE HOLLOW ORGAN

[75] Inventor: Heinrich Planck, Nurtingen, Fed. Rep. of Germany

[73] Assignee: Institute fur Textil-und Faserforschung of Stuttgart, Nurtingen, Fed. Rep. of Germany

[21] Appl. No.: 267,362

[22] Filed: May 26, 1981

[51] Int. Cl.⁴ ............................. A61F 2/06; A61F 2/04
[52] U.S. Cl. ............................................ 623/1; 623/12
[58] Field of Search ................ 3/1, 1.4; 128/334 R, 128/334 C; 138/123, 124; 623/1, 11, 12

[56] References Cited

U.S. PATENT DOCUMENTS

| | | | |
|---|---|---|---|
| 2,977,839 | 4/1961 | Koch | 138/123 X |
| 3,105,492 | 10/1963 | Jeckel | 3/1.4 X |
| 3,304,557 | 2/1967 | Polansky | 3/1.4 |
| 3,463,158 | 8/1969 | Schmitt et al. | 3/1.4 X |
| 3,479,670 | 11/1969 | Medell | 3/1.4 |
| 3,485,234 | 12/1969 | Stevens | 138/123 X |
| 3,562,820 | 2/1971 | Braun | 3/1.4 |
| 3,580,289 | 5/1971 | James et al. | 138/123 X |
| 3,974,526 | 8/1976 | Dardik et al. | 3/1.4 |
| 4,044,404 | 8/1977 | Martin et al. | 3/1.4 X |
| 4,086,665 | 5/1978 | Poirier | 3/1.4 |

FOREIGN PATENT DOCUMENTS 2033233A 5/1980 United Kingdom .................. 3/1.4

Primary Examiner—Ronald L. Frinks
Attorney, Agent, or Firm—Antonelli, Terry & Wands

[57] ABSTRACT

A flexible hollow organ, especially a vascular prosthesis intended for implantation in the human or animal body parts. The hollow organ includes a flexible prosthetic tube serving for a throughflow of a medium or which consists of such a prosthetic tube. A wall of the prosthetic tube exhibits at least one braided hose of flexible, elastic threads produced as a hollow meshwork. The hose, where provided, imparts to the prosthetic tube an increased resistance against buckling and compression.

40 Claims, 2 Drawing Sheets

FLEXIBLE HOLLOW ORGAN

The present invention relates to a flexible hollow organ and, more particularly, to a vascular prosthesis intended for implantation in a human or animal body, which comprises a flexible prosthetic tube serving for a throughflow of a medium or which consists of such a prosthetic tube.

A hollow organ of the aforementioned type is proposed in, for example, Offenlegungsschrift 2,806,030, with the hollow organ serving as a tube for artificial blood vessels and consisting of glued-together individual fibers oriented at least in one preferential direction. It has also been proposed to provide prosthetic blood vessel tubes which consist of hosiery-type, knitted, or woven porous hoses as well as prosthetic blood vessel tubes of microporous expanded polytrafluoroethylene.

A common disadvantage of all of the proposed artificial blood vessel tubes resides in the fact that they exhibit a relatively large "critical bending radii", which is understood to means a radius of a size which must not be any smaller in order to avoid an occurrence of a buckling of the prosthetic tube. As can readily be appreciated, a buckling would lead to a strong reduction of the free interior cross section or even to an occlusion of the prosthetic tube.

In order to reduce the "critical bending radius", it has been proposed to wind a spiral of a synthetic resin around the vascular prosthetic tube however, a disadvantage of this proposal resides in the fact that the spiral must be produced from a relatively thick monofilmanet in order to be able to fulfill its function and, consequently, can present a considerable disturbance in the body. Additionally, the manufacture of this proposed arrangement as well as the administration thereof are difficult and time-consuming.

The aim underlying the present invention essentially resides in providing a hollow organ of the aforementioned type wherein the prosthetic tube exhibits, at least along a section of its length, smaller critical bending radii without substantially changing a wall thickness of the prosthetic tube.

In accordance with advantageous features of the present invention, a wall of the prosthetic tube includes at least one braided hose of flexible, elastic threads fashioned in the form of a hollow meshwork, with the braided hose imparting to the prosthetic tube along its zone an increased resistance against buckling and compression.

By virtue of the provision of the braided hose fashioned as hollow meshwork, there is a reduction, in its zone, of the critical radius of curvature of the prosthetic tube to a considerable extent so that it is possible to attain very small critical radii of curvature. Additionally, the braided hose increases the resistance of the prosthetic tube considerably against other cross sectional constrictions and this is made possible without having to appreciably enlarge a wall thickness of the prosthetic tube.

Furthermore, the prosthetic tube of the present invention remains rather flexible and can be produced to be even more flexible than the above-noted vascular prosthetic tube reinforced by a spiral. Additionally, by viture of the measures proposed by the present invention for reducing the radius of curvature, a hollow organ is provided which is more economical than the above-noted prosthetic tube reinforced by the spiral.

The prosthetic tube of the present invention may be utilized in numerous applications in the human and animal body and, preferably, the tube may be used in the form of a blood vessel prosthesis, an esophageal or tracheal prosthesis, an artificial ureter or urethra, or an artificial bile duct. It is also possible to use the prosthesis tube as an intestine prosthesis. As can readily be appreciated, still further uses may be contemplated.

Preferably, in accordance with the present invention, the braided hose consists of metallic threads; however, it is also advantageous, in many situations, to braid the hose of polymeric synthetic resin filaments and/or a mixture of metallic threads and polymeric synthetic resin filaments.

By virtue of the provision of the metallic threads, it is possible to produce a braided hose with an especially thin wall. Preferably, the metallic threads may have diameters of 0.04–0.15 mm and, especially about 0.05–0.07 mm. If synthetic resin filaments are utilized for the braided hose, the synthetic resin filaments may suitably have diameters of 0.05–1.0 mm and, preferably, about 0.04 mm.

The braided hose may be arranged on the prosthetic tube in various manners and, preferably, the hose may be located in an interior wall of the prosthetic tube by, preferably, being embedded therein.

In many cases it is also advantageous in accordance with the present invention to dispose the braided hose in an inner surface of the wall of the prosthetic tube, especially if it is desired to thereby also impart a certain roughness to an inside surface of the prosthetic tube. However, if the braided hose is arranged on the outer surface of prosthetic tube which may likewise be advantageous in many instances, then the body tissue can grow into this hose after implantation and thus the hose may improve and secure the anchorage of the prosthetic tube within the body.

It is also possible in accordance with the present invention to subsequently provide an existing conventional prosthetic tube with an externally applied braided hose in the present invention so as to reduce, in particular, the critical bending radius.

While it is possible to provide a braided hose over a full axial length of the prosthetic tube, in many instances, it is sufficient or even advantageous to equip merely one or several predetermined longitudinal sections of the prosthetic tube with a braided hose so as, for example, to provide, in the case of an artificial blood vessel tube which is to be extended through a joint such as, for example, an elbow or a knee, that the braided hose is located after implantation only in the region of the joint.

It is also possible in accordance with the present invention to arrange several braided hoses at longitudinal mutual spacings along the prosthetic tube and, in some situations, it may also be expedient to provide that a braided hose is encompassed by at least one further braided hose either snuggly or with a spacing to, for example, obtain special bending characteristics.

In some situations it may be suitable to encircle a braided hose of the present invention by a substantially shorter second braided hose only along a portion of the length of the first braided hose such as, for example, along a central zone, to additionally secure against buckling and extensive cross sectional contriction a zone at which the highest buckling risk exists or a zone which is exposed to an especially high external pressure.

Advantageously, in accordance with the present invention, at least a partial number of the threads of the braided hose and, preferably, all of the threads are monofilaments since, in this manner, the braided hose is then provided with an expecially high bending elasticity so that, even in the case of extreme deformations, the hose returns to its original shape upon cesation of the deformation load. In this connection, a monofilament is to be understood as a filament consisting of a single elementary thread, that is, which, in case of a polymeric monofilled synthetic resin thread, has been spun from the orifice of a spinneret or, in the case of a monofilament metallic thread, has been drawn as a thin wire from a drawing die of a drawing tool.

The remaining material of the prosthetic tube beside the braided hose or hoses may, in accordance with the present invention, made of a conventional material. Thus, for example, the prosthetic tube may have at least one tubular woven, hosiery-type, or knit fabric or may be a nonwoven mat of textile fibers. However, it is also possible to fashion the prosthetic tube so that it consists of a synthetic resin hose and, preferably, an expanded polytetrafluoroethylene, polyether urethane, or a silicone elastomer, and the braided hose.

In order to counteract a rejection of the prosthetic tube by the human or animal body, to lessen such rejection, or to make such rejection more easily controllable, in accordance with the present invention, at least one tubular layer of the prosthetic tube may consist of animal or human tissue, preferably, the tissue of an umbilical cord.

It is especially advantageous in accordance with the present invention to braid the hollow meshwork constituted in the braided hose in a linen weave so thereby the threads of the braided hose support one another and provide an inherent elasticity and also an especially high elastic recovery.

Generally, it is also desirable that the tubular prostheses withstand considerable torsional movements without a change in cross section or almost without a cross-sectional variation, that is, that the tubular prosthesis has a high torsional stability. For this purpose, in accordance with further features of the present invention, it is possible to establish a braiding angle, that is, an intersecting angle of the groups of threads, halved by the longitudinal plane of symmetry of the hollow meshwork, of the braided hose to be 60° to 160° and, preferably, to be 70°–110° so that the prosthetic tube offers especially strong resistance to torsional movements.

The hollow organ may consist of a tubular prothesis or may still have further parts in addition to the tubular prothesis. More particularly, the hollow organ may, for example, be made of a prosthetic tube with a built-in flap valve for use as a cardiovascular prosthesis. Alternatively, mouth pieces or other additional parts may be attached to the tubular prothesis.

Accordingly, it is an object of the present invention to provide a prosthesis which avoids, by simple means, shortcomings and disadvantages encountered in the prior art.

Another object of the present invention is to provide a prosthetic tube which has, at least along one section of its axial length, a smaller critical bending radii.

Yet another object of the present invention resides in providing a prosthetic tube which is even more flexible than previously proposed prosthetic tubes.

A still further object of the present invention resides in providing a prothesis which is simple in construction and therefore relatively inexpensive to manufacture.

These and other objects, features, and advantages of the present invention will become more apparent from the following description when taken in connection with the accompanying drawings which show, for the pruposes of illustration only, several embodiments in accordance with the present invention, and wherein.

Figure 1:
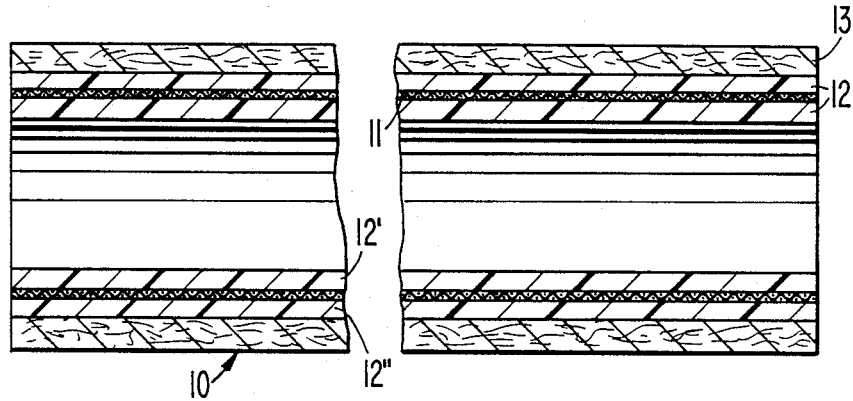
FIG. 1 is a longitudinal cross sectional view of a tubular prosthesis constructed in accordance with the present invention.

Referring now to the drawings wherein like reference numerals are used throughout the various views to designate like parts and, more particularly, to FIG. 1, according to this figure, a tubular prosthesis generally designated by the reference numeral 10 may have, for example, a round or other section which is constant over its entire axial length. The tubular prosthesis 10 is elastically flexible and includes two mutually coaxial tubular layers 12, 13, with the inner layer 12 being made of a polymeric elastic synthetic resin and constituting a flexible tubing which is embedded in a braided hose 11 extending over an entire length of the tubular prosthesis 10. The braided hose 11 is coaxial to the layer 12 in which it is embedded and subdivides the layer practically into two sublayers 12', 12''. However, the braided hose 11 is braided in such a manner that its groups of threads leave small rhomboid perforations between them so that the two sublayers 12', 12'' are fixedly joined together through synthetic resin bridges integral with the sublayers 12', 12'', which bridges extend through the rhomboid perforations of the braided hose. In this manner, the two sublayers 12', 12'', practically form a single tubular layer with the embedded braided hose 11.

The tubular layer 12 is encompassed by the tubular outer layer 13 secured thereto by, for example, adhesives. The outer layer 13 consists of mutually cemented-together textile fibers oriented in one or several preferential directions and extending obliquely to a circumferential direction of the tubular prosthesis 10. The outer layer 13 may be manufactured in the manner described, for example, in aforementioned Offenlegungsschrift 2,806,030.

After implantation, body tissue can grow into the tubular prosthesis 10 which, for example, may be an artificial blood vessel. The growth of the body tissue into the tubular prosthesis 10 takes place due to the porous nature of the outer layer 13 which forms a fiber mat.

The tubular prosthesis 10 of FIG. 1 may, for example, be manufactured in the following manner:

A rod of wax of circular cross section and a 6 mm diameter serves as a core, with the rod of wax being dipped into a polyurethane solution of, for example, 10% by weight polyurethane dissolved in dimethylformamide so as to obtain a homogeneous layer of polyurethane. After the layer of polyurethane has dried, a prefabricated hollow meshwork of an elastic stainless steel threads of, for example, V4A wire having a diameter of 0.06 mm and a circular cross section is applied to the dry layer. The hollow mesh work has a construction of 40 braider bobbins, linen weave, and 30 braids per cm. The rod is then again dipped into the 10% by weight polyurethane solution and thereupon a nonwoven layer of polyurethane fibers is applied in the manner proposed in Offenlegungsschrift 2,806,030 by spraying a polyurethane solution of 8% by weight of polyurethane dimethylformamide with the aid of compressed air. After a drying of the layer, the wax rod is removed by melting the same and the tubular prosthesis 10 is thus finished. The tubular prosthesis 10 is soft elastic flexible and has a very small critical radius of curvature.

Figure 2:
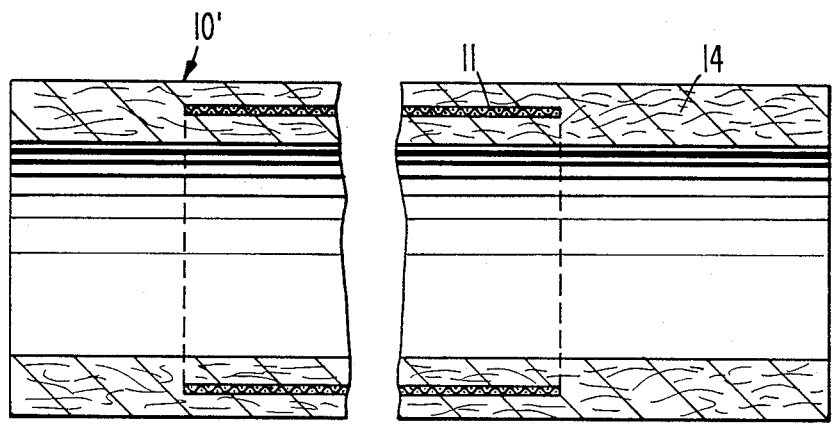
FIG. 2 is a longitudinal cross sectional view of a second embodiment of a tubular prosthesis in accordance with the present invention.

As shown in FIG. 2, a tubular prosthesis generally designated by the reference numeral 10' consists of an elastic flexible porous tube body 14 formed of glued together textile fibers having a preferential orientation in one or several directions and extending obliquely to a circumferential direction of the tube body 14. The substantially shorter braided hose 11 is embedded in a central zone of the tube body 14. The shorter braided hose 11 may, for example, be composed of monofiltype thin metal filaments.

The tubular prosthesis 10' may, for example, be manufactured in the following manner:

A wax rod having a length of 50 cm and a circular cross section with a diameter of 4 mm is provided as described in the aforementioned Offenlegungsschrift 2,806,030, with a polyurethane fiber mat by a spraying of a polyurethane solution by means of compressed air. The polyurethane solution consists of 8% by weight of polyurethane dissolved in a mixture of dimethylformamide/acetone 4:1. The fiber mat extends over the length of the wax rod. Thereupon a prefabricated hollow meshwork is applied as the braided hose 11 made up of polyester terephthalate monofils of a circular cross section having a diameter of 0.1 mm. The construction of the meshwork is 32 braider bobbins, linen weave, 15 braids per cm and, in the embodiment of FIG. 2, the hose 11 has an axial length of 10 cm. The braided hose 11 is arranged in a longitudinal center of the wax rod and subsequently another layer of polyurethane fiber mat is applied in the same way as described above. The was rod is then dissolved by melting and the tubular prosthesis 10' is finished. A wall thickness of the two mat layers of the prosthetic tube are respectively 0.3 mm with a total wall thickness being 8 mm. A critical bending radius of the tubular prothesis 10' would amount to about 20 mm without the braided hose 11; however, with the braided hose 11 the critical bending radius is reduced to a mere 2 mm.

Figure 3:
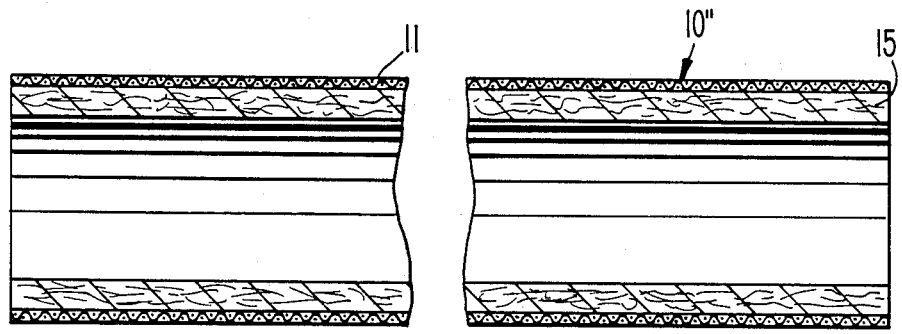
FIG. 3 is a longitudinal cross sectional view of a third embodiment of a tubular prosthesis in accordance with the present invention.

FIG. 3 provides an example of a further prosthetic tube generally designated by the reference numeral 10" which consists of a prefabricated conventional knit type tubular double-velour prosthesis 15 on which is applied a braided hose 11 produced as a hollow meshwork. The prosthetic tube 10" may, for example, be manufactured in the following manner:

The braided hose 11 may consist of, for example, polyester terephthalate monofils of a circular cross section with a diameter of 0.2 mm. The construction of the meshwork is 48 braider bobbins, linen weave, 15 braids per cm with an internal diameter of 12 mm. The braided hose 11 is heated directly prior to an application to the prosthesis 15 to a temperature of 195° C. and thermal fixed for about 5 minutes at such temperature. The braided hose 11 is subsequently pulled onto the prothesis 15 and then additionally glued thereto in a spotwise manner by means of a suitable adhesive such as, for example, a silicone elastomer adhesive (medical braid). Advantageously, four glue spots are provided per cm of length and are uniformly distributed along the circumference.

Instead of applying a prefabricated hollow meshwork as the braided hose 11 to the prosthesis 15 it is also possible for the prosthesis 15 to be initially placed flush on a circular cylindrical rod with the rod then being pushed at a uniform rate through a central bore of a wire braiding machine so that the prosthesis 15 present on the rod is provided with a braided hose produced therearound. In a production of a tubular prosthesis conducted as an experiment, the braiding machine had 32 braider bobbins provided with respectively one monofil type titanium thread of circular cross section in a diameter of 0.1 mm. The feed rate of the rod was adjusted so that 17 braids per cm of length were formed.

As with the previous embodiments, the tubular prosthesis 10" is elastically flexible and has very small critical radii of curvature.

Figure 4:
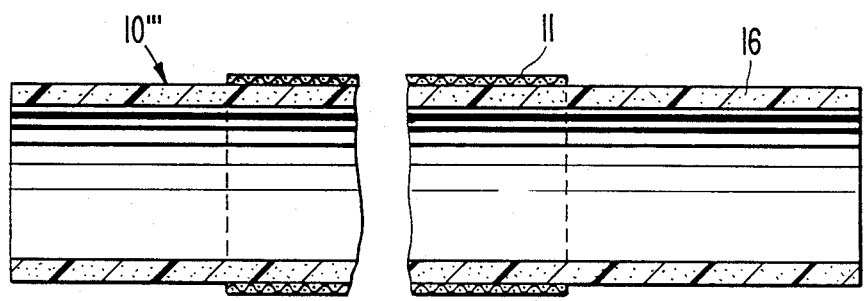
FIG. 4 is a longitudinal cross sectional view of a fourth embodiment of a tubular prosthesis in accordance with the present invention.

FIG. 4 provides yet another example of a prosthetic tube generally designated by the reference numeral 10''' which consists of a tube 16 of a microporous expanded polytetrafluoroethylene. An essentially shorter braided hose 11 is placed on the tube 16 only in a central longitudinal zone thereof, with the braided hose 11 being fixedly mounted thereon by spot-like glue points.

While the tubular prosthesis 10, 10', 10'', and 10''' illustrated in FIGS. 1–4 have constant cross sections over their entire length, which cross sections are preferably round, as can readily be appreciated, it is also possible to fashion the cross sections so as to be non-uniform over the length thereof. It is also possible to utilize the present invention optionally in a tubular prosthesis having tubular branches such as, for example, a bifurcation of the tube into two further extending smaller tubes.

While I have shown and described several embodiments in accordance with the present invention, it is understood that the same is not limited thereto but is susceptible of numerous changes and modifications as known to one having ordinary skill in the art, and I therefore do not wish to be limited to the details shown and described herein, but intend to cover all such modifications as are encompassed by the scope of the appended claims.

I claim:

1. A prosthesis for implantation in a human or animal body, the prosthesis comprising a flexible non-corrugated prosthetic tube means for a throughflow of a medium, and at least one flexible elastic braided hose means is arranged along at least a portion of a wall of the tube means for imparting an increased resistance against buckling and compression to the tube means thereby reducing a critical bending radius of the prosthesis, the at least one braided hose means is formed as a hollow meshwork braided in a linen weave mode with a braiding angle of the braided hose means being in a range of 60°–160°.

2. A prosthesis according to claim 1, wherein the braiding angle is in the range of 70° to 110°.

3. A prosthesis for implantation in a human or animal body, the prosthesis comprising a flexible non-corrugated prosthetic tube means for a throughflow of a medium and at least one flexible elastic braided hose means arranged along at least a portion of a wall of the tube means for imparting an increased resistance against buckling and compression to the tube means thereby reducing a critical bending radius of the prosthesis, the tube means includes at least two mutually coaxial tubular layers, said at least one flexible elastic braided hose means formed as a hollow meshwork is embedded in said tube means, and the braided hose means is arranged in one of the tubular layers so as to substantially subdivide the same into two sublayers.

4. A prosthesis for implantation in a human or animal body, the prosthesis comprising a flexible non-corrugated prosthetic tube means for a throughflow of a medium, and at least one flexible elastic braided hose means formed as a hollow meshwork is arranged along at least a portion of a wall of the tube means for imparting an increased resistance against buckling and compression to the tube means thereby reducing a critical bending radius of the prosthesis, the hose means formed as a hollow meshwork is braided in such a manner so as to have substantially rhomboidal perforations between threads thereof so as to enable material of the tube means to be accommodated in the perforations.

5. A prosthesis according to one of claims 1, 3 or 4, wherein the hollow meshwork is composed of metallic threads.

6. A prosthesis according to claim 5, wherein the metallic thread consists essentially of one of stainless steel or titanium.

7. A prosthesis according to claim 6, wherein the metallic threads have a diameter of between 0.04–0.15 mm.

8. A prosthesis according to claim 5, wherein the diameter of the metallic threads is between 0.05 and 0.07 mm.

9. A prosthesis according to one of claims 1, 3 or 4, wherein the hollow meshwork is composed of polymeric synthetic resin.

10. A prosthesis according to one of claims 1, 3 or 4, wherein the hollow meshwork is composed of metallic threads and synthetic resin threads.

11. A prosthesis according to claim 10, wherein the metallic threads have a diameter of between 0.04–0.15 mm.

12. A prosthesis according to claim 10, wherein the synthetic resin threads of the hose means have a diameter of between 0.05–1 mm.

13. A prosthesis according to one of claims 1, 3, or 4, wherein the braided hose means is arranged on an inner surface of the wall of the tube means.

14. A prosthesis according to one of claims 1, 3, or 4, wherein at least some of the threads of said hose means are monofilaments.

15. A prosthesis according to claim 14, wherein all of the threads of said hose means are monofilaments.

16. A prosthesis according to one of claims 1, 3 or 4, wherein the tube means includes at least one tubular mat of glued-together textile fibers.

17. A prosthesis according to one of claims 1, 3 or 4, wherein the tube means is a synthetic resin tube.

18. A prosthesis according to one of claims 1, 3 or 4, wherein the hose means extends only over a portion of an axial length of the tube means.

19. A prosthesis according to one of claims 1, 3 or 4, wherein a plurality of hose means are provided and are arranged along a tube means at an axial spacing from one another.

20. A prosthesis according to one of claims 1, 3 or 4, wherein the prosthesis is an artificial blood vessel.

21. A prosthesis according to one of claims 1, 3 or 4, wherein the prosthesis is one of an artificial esophagus or trachea.

22. A prosthesis according to one of claims 1, 3 or 4, wherein the prosthesis is one of an artificial ureter or urethra.

23. A prosthesis according to one of claims 1, 3 or 4, wherein the prosthesis is an artificial bile duct.

24. A prosthesis according to one of claims 1, 3 or 4, wherein the prosthesis is an artificial intestine.

25. A prosthesis according to one of claims 1 or 4, wherein the braided hose means is arranged in one of a plurality of tubular layers so as to substantially subdivide the same into two sublayers.

26. A prosthesis according to claim 25, wherein the hose means is braided in such a manner so as to have substantially rhomboidal perforations between threads thereof thereby enabling material of the two sublayers to be accommodated in the perforations.

27. A prosthesis according to one of claims 1, 3 or 4, wherein the tube means is formed as an elastic flexible porous member, and the flexible elastic braided hose means is embedded in the porous member.

28. A prosthesis according to one of claims 1, 3 or 4, wherein the tube means is formed as a microporous member, the flexible elastic braided hose means is arranged at least in a longitudinal center area thereof.

29. A prosthesis according to one of claims 1, 3 or 4, wherein the tube means includes at least two mutually coaxial tube layers, an outer layer of the tube layers is porous and includes textile fibers joined together by an adhesive with the fibers being oriented in at least a direction obliquely to a circumferential direction of the tube means.

30. A prosthesis according to one of claims 1 or 4, wherein the braided hose means is arranged on an other surface of the tube means.

31. A prosthesis according to one of claims 1 or 4, wherein the braided hose means is arranged inside of the wall of the tube means.

32. A prosthesis according to claim 31, wherein the braided hose means is embedded in the wall of the tube means.

33. A prosthesis according to one of claims 1 or 3, wherein the tube means includes at least two mutually coaxial tubular layers, said at least one flexible elastic braided hose means is embedded in said tube means.

34. A prosthesis according to claim 33, wherein the braided hose means is coaxially disposed with respect to the tubular layers.

35. A prosthesis according to one of claims 1 or 3, wherein the hose means is braided in such a manner so as to have substantially rhomboidal perforations between threads thereof so as to enable material of the tube means to be accommodated in the perforations.

36. A prosthesis according to one of claims 1, 3 or 4, wherein a flap valve means is arranged in a prosthetic tube for forming a cardio-vascular prosthesis.

37. A prosthesis according to claim 46, wherein the braided hose means is coaxially disposed with respect to the tubular layers.

38. A prosthesis according to one of claims 1, 3 or 4, wherein the tube means includes at least one tubular woven cloth.

39. A prosthesis according to one of claims 1, 3 or 4, wherein the tube means includes at least tubular knitted cloth.

40. A prosthesis according to one of claims 1, 3 or 4, wherein said tube means includes at least one tubular hosiery-type cloth.

* * * * *

UNITED STATES PATENT AND TRADEMARK OFFICE
CERTIFICATE OF CORRECTION

PATENT NO.   : 4,850,999
DATED        : July 25, 1989
INVENTOR(S)  : Heinrich PLANCK It is certified that error appears in the above-identified patent and that said Letters Patent is hereby corrected as shown below:

ON THE TITLE PAGE

[73] Assignee   Institute fur Textil-und
                Faserforschung of Stuttgart,
                Denkendorf, Fed. Rep. of Germany Signed and Sealed this Fourteenth Day of January, 1992

Attest:

HARRY F. MANBECK, JR.

*Attesting Officer*   *Commissioner of Patents and Trademarks*